United States Patent

Ao et al.

[11] Patent Number: 5,965,731
[45] Date of Patent: Oct. 12, 1999

[54] PRODUCTION OF TRIS(2,4,6-TRIBROMOPHENOXY)-S-1,3,5-TRIAZINE

[75] Inventors: Meng-Sheng Ao; Billie B. Dadgar; Phillip R. Beaver, all of Baton Rouge; Mark W. Beltz, Prairieville, all of La.

[73] Assignee: Albemarle Corporation, Richmond, Va.

[21] Appl. No.: 09/146,155

[22] Filed: Sep. 3, 1998

[51] Int. Cl.$^6$ .................................................. C07D 251/30
[52] U.S. Cl. .............................................................. 544/219
[58] Field of Search ............................................. 544/219

[56] References Cited

U.S. PATENT DOCUMENTS

| 3,843,650 | 10/1974 | Pews et al. | 260/248 |
| 3,950,306 | 4/1976 | Pews et al. | 260/45.8 |

FOREIGN PATENT DOCUMENTS

| 1566675 | 3/1969 | France . |

OTHER PUBLICATIONS

Thurston, et al., "Cyanuric Chloride Derivatives. I. Aminochloro–s–triazines", Journal of the Am. Chemical Society, Jul. 6, 1951, vol. 73, no. 7, pp. 2981–3008.

Degussa Specification Sheet, "Cyanuric Chloride", May 5, 1995, 1 page.

Degussa Corporation, Material Safety Data Sheet, May 9, 1996, pp. 1–5.

*Primary Examiner*—John M. Ford
*Attorney, Agent, or Firm*—E. E. Spielman, Jr.

[57] ABSTRACT

In an aqueous reaction medium, phenol is brominated with bromine under conditions forming an aqueous hydrobromic acid phase and an organic phase consisting essentially of molten 2,4,6-tribromophenol. The aqueous hydrobromic acid phase and the molten 2,4,6-tribromophenol are separated from each other, and optionally the molten 2,4,6-tribromophenol is washed with an aqueous decolorizing solution. An alkali metal base and water are mixed with the 2,4,6-tribromophenol to form an alkali metal salt of tribromophenol. Then, in a mixture consisting essentially of water and at least one liquid ketone, cyanuric chloride is reacted with at least a portion of the alkali metal 2,4,6-tribromophenolate of such that tris(2,4,6-tribromophenoxy)-s-1,3,5-triazine is produced.

29 Claims, No Drawings

PRODUCTION OF TRIS(2,4,6-TRIBROMOPHENOXY)-S-1,3,5-TRIAZINE

BACKGROUND

The compound, tris(2,4,6-tribromophenoxy)-s-1,3,5-triazine, was reported in French Patent 1,566,675, in 1969. The compound is useful as a flame retardant. In U.S. Pat. Nos. 3,843,650 and 3,950,306 a process for the production of tris(2,4,6-tribromophenoxy)-s-1,3,5-triazine is described. In addition, two recommended processes utilize the reaction of cyanuric chloride and 2,4,6-tribromophenol in the presence of either sodium carbonate and methyl ethyl ketone or aqueous sodium hydroxide and acetone. The product has poor solubility in ketone solvents and is readily removed by filtration. When sodium hydroxide is used as the base, water is formed as a by-product; sodium bicarbonate or carbon dioxide is formed when sodium carbonate is used. While workable, the foregoing processes are not as efficient as desired.

SUMMARY OF THE INVENTION

This invention relates to novel process technology which enables highly efficient, cost-effective production of tris(2,4,6-tribromophenoxy)-s-1,3,5-triazine of commercially satisfactory color in essentially quantitative yields. This novel technology is exceptionally well suited for use in large scale commercial plant facilities. Moreover, the process technology is environmentally friendly.

An embodiment of this invention is a process for the production of tris(2,4,6-tribromophenoxy)-s-1,3,5-triazine, using bromine and phenol as the initial reactants, which process comprises:

a) in an aqueous reaction medium, brominating phenol with bromine under conditions effective to form an aqueous hydrobromic acid phase and an organic phase consisting essentially of molten 2,4,6-tribromophenol;

b) separating the aqueous hydrobromic acid phase and the molten 2,4,6-tribromophenol from each other, and optionally washing the molten 2,4,6-tribromophenol with an aqueous decolorizing solution;

c) mixing an alkali metal base and water with at least a portion of the 2,4,6-tribromophenol of b) to form an alkali metal salt of tribromophenol; and d) in a mixture of water and at least one liquid ketone, reacting cyanuric chloride with at least a portion of the alkali metal 2,4,6-tribromophenolate of c) such that tris(2,4,6-tribromophenoxy)-s-1,3,5-triazine is produced.

Besides the advantages referred to above, at least a), b) and c) of the process can be, and preferably are, performed in the same reaction vessel without removal of the 2,4,6-tribromophenol therefrom. Indeed, in a particularly preferred embodiment d) above is also performed in the same reaction vessel. Moreover, almost no waste co-product is formed in the process—only some innocuous NaCl. Thus, the process is environmentally friendly. For example, in step a) the HBr co-product is absorbed by the water unless and until the water is saturated, and additional quantities, if any, are evolved as gas. Such aqueous HBr and gaseous HBr, if any, are collected for use in chemical synthesis operations or for sale for such use. And, ketone used in step d) can be, and preferably is, recovered and recycled.

Preferably, the alkali metal 2,4,6-tribromophenolate and the cyanuric chloride are proportioned such that there is a small excess of the alkali metal 2,4,6-tribromophenolate. In this way, undesirable side reactions are avoided or at least kept to a minimum. Moreover, the ketone keeps the excess or any unreacted alkali metal 2,4,6-tribromophenolate in solution and makes possible a clean separation between the tris(2,4,6-tribromophenoxy)-s-1,3,5-triazine product and the alkali metal 2,4,6-tribromophenolate and other ketone-soluble impurities, if any, present in the final reaction product mixture.

These and other embodiments and advantages of this invention will become still further apparent from the ensuing description and appended claims.

FURTHER DETAILED DESCRIPTION

Step a)

The first step of the process is bromination of phenol in an aqueous medium. By conducting this reaction in water, 2,4,6-tribromophenol is formed in a fast and clean reaction which requires no catalyst. When suitably conducted, both conversion and yield can be over 99%. The bromination is exothermic and cooling is needed to regulate the reaction temperature. Preferably, at ambient temperature bromine is fed into a mixture of phenol and water, although other modes of addition can be used, such as concurrent (continuous or intermittent) feeds of phenol and bromine into water. The proportions of the reactants should be in the range of about 3 to about 3.3 equivalents (moles) of bromine ($Br_2$) per equivalent (mole) of phenol. As to temperature, it is preferable when feeding the bromine into the mixture of phenol and water, to allow the temperature to raise from ambient room temperature to about 45–65° C., preferably to about 50 to about 60° C. (e.g., ca. 50° C.) during about the first 60% of the addition. During the rest of the addition, the temperature is allowed (or if necessary, caused) to elevate up to about 90–100° C., most preferably up to about 100° C., so that the product 2,4,6-tribromophenol is in the molten state. Bromine feed should be slow enough to keep the bromine in the reaction mixture, and, thus, it is preferred to control the rate at which the liquid bromine is fed and the temperature of the reaction mixture such that substantially no bromine vapor is formed in the reaction vessel during substantially the entire reaction period.

The amount of water used in the bromination does not affect the chemistry, but affects the product color, the HBr recovery and reactor loading. When the bromination was conducted using a weight ratio of 3 parts of water to 1 part of phenol, 2,4,6-tribromophenol of good color properties was formed. Also, only aqueous HBr (48%) solution was the co-product; no gaseous HBr was evolved. When the bromination was conducted using a weight ratio of 1 part of water to 1 part of phenol, 2,4,6-tribromophenol product of good quality was again produced, and in this case, the co-products were aqueous HBr (60%) and gaseous HBr. However, when the quantity of water was only 8% by weight of the weight of the phenol used, the bromination needed 20% by weight more bromine and the color of the 2,4,6-tribromophenol product from this low water run was poor. Therefore, it is preferred to use at least about an equal amount by weight of water and phenol (e.g., the amount of water is in the range of about 1 to about 10 parts by weight per part by weight of phenol), because under these conditions, 2,4,6-tribromophenol product of good quality is produced. Most preferably, the amounts by weight of water and phenol are about equal (i.e., the weight ratio is ca. 1±0.1). In this case, both aqueous and gaseous HBr will be formed, but the reactor loading is higher and, thus, plant throughput is increased per unit of time, and the recovered gaseous HBr can be effectively utilized for other purposes. The recovered aqueous HBr can be used in the next bromination. Such recycle has been carried out and found to produce no ill effects on the process or product quality.

Step b)

At the end of the reaction of step a), the hydrobromic acid is separated from the reaction mass by a phase separation procedure, e.g., by draining off the lower phase or decanting off the upper phase, or by use of other suitable physical separation procedures.

Optionally, but preferably, the hot molten 2,4,6-tribromophenol is treated with a suitable decolorizing agent such as an aqueous solution of hydrazine or of an alkali metal sulfite (e.g., $Na_2SO_3$ or $K_2SO_3$) to remove color. Typically, this decolorization operation is conducted at a temperature in the range of about 90 to about 100° C. so that the 2,4,6-tribromophenol remains in the liquid state. The hydrazine can be employed as neat liquid or as an aqueous solution of any concentration, but typically will be used as an aqueous solution containing about 20 to about 50 wt % of hydrazine, and preferably about 35 wt % of hydrazine. Sodium or potassium sulfite is typically employed as a 1 to about 15 wt % aqueous solution. Other suitable decolorizing agents can be used, the only requirement being that the decolorizing agent must not destroy any appreciable quantity of the 2,4,6-tribromophenol under the decolorization conditions employed. Because the amount of decolorizing agent used is so small, it poses no problem with respect to waste product treatment or disposal.

Step c)

Step b) is followed by treatment of the 2,4,6-tribromophenol with an alkali metal base of sufficient basicity to form an alkali metal salt of the 2,4,6-tribromophenol. Examples of suitable water-soluble alkali metal bases include lithium hydroxide, lithium oxide, lithium carbonate, sodium hydroxide, sodium oxide, sodium carbonate, potassium hydroxide, potassium oxide, potassium carbonate, and similar inorganic alkali metal bases. While the base can be added as a solid to a mixture of water and 2,4,6-tribromophenol, it is preferable to mix or otherwise contact the 2,4,6-tribromophenol with an aqueous solution of the alkali metal base, and most preferably with an aqueous solution of caustic (formed by dissolving sodium hydroxide or sodium oxide in water) to form the sodium salt of 2,4,6-tribromophenol in an aqueous medium. If an optional but preferred decolorization operation of step b) was used, most preferably the conversion of the 2,4,6-tribromophenol into its alkali metal salt is performed in the same aqueous medium as that in which the decolorization operation was performed.

Typically, the reaction between the 2,4,6-tribromoplienol and the alkali metal base is conducted at a temperature in the range of about 20 to about 100° C. The reaction involves one equivalent of alkali metal per equivalent of 2,4,6-tribromophenol, and thus, if either reactant is used at a ratio of equivalents of less than 1, it becomes the limiting reactant. Thus, the amount of base used is preferably in the range of about 0.9 to about 1.0 equivalent of alkali metal per equivalent (mole) of 2,4,6-tribromophenol. It will be understood, of course, that, for example, one equivalent of NaOH relative to 1 mole of 2,4,6-tribromophenol is 1 mole of NaOH, whereas one equivalent of $Na_2CO_3$ relative to 1 mole of 2,4,6-tribromophenol is 0.5 mole of $Na_2CO_3$.

Step d)

In this step sodium salt of 2,4,6-tribromophenol from c) is reacted with cyanuric chloride in a mixture of water and at least one ketone to form tris(2,4,6-tribromophenoxy)-s-1,3,5-triazine. Cyanuric chloride, a solid compound at ambient room temperature conditions, can be introduced into the reaction mixture in three ways; as a solution in a solvent, as solid in powder form, or as liquid in molten phase. It has been found that it is best to introduce a solution of the cyanuric chloride in a ketone, preferably acetone, to a refluxing aqueous solution of sodium 2,4,6-tribromophenolate. This mode of addition results in the rapid formation of tris(2,4,6-tribromophenoxy)-s-1,3,5-triazine, and the product purity is good. It has also been demonstrated that cyanuric chloride can be added in powdered form to the reaction mixture. When added as a powder at room temperature, refluxing for 2 hours was required to form the tris(2,4,6-tribromophenoxy)-s-1,3,5-triazine product, and the product was found to be contaminated with 2–3% of bis(2,4,6-tribromophenoxy)(chloro)-s-1,3,5-triazine impurity. And, when adding molten cyanuric chloride (mp 148° C.) at 160° C. to the refluxing sodium 2,4,6-tribromophenolate mixture, in addition to the formation of the desired tris(2,4,6-tribromophenoxy)-s-1,3,5-triazine product, the reaction formed about 10% of a hydrolysis by-product, viz., bis-(tribromophenoxy)-hydroxy-s-1,3,5-triazine as an impurity. Therefore, while introduction of the cyanuric chloride in molten condition is operable, it is the least preferred mode of addition. More preferred is the addition of the cyanuric chloride in finely divided or powdery form. The most preferred mode of addition is to introduce the cyanuric chloride as a solution in a liquid ketone, such as acetone.

Preferably, the reactants are proportioned such that there is a small excess of the alkali metal 2,4,6-tribromophenolate relative to the cyanuric chloride. Ordinarily, an excess of up to about 2 mole % of the alkali metal 2,4,6-tribromophenolate over the stoichiometric amount required to react with the amount of cyanuric chloride used is suitable for achieving the avoidance or minimization of undesirable by-products.

It has been found that a liquid ketone such as acetone or methyl ethyl ketone when present in this reaction mixture tends to ensure that the desired tris(2,4,6-tribromophenoxy)-s-1,3,5-triazine product is formed in high purity. In experiments wherein a refluxing mixture of water and an alkanol (methanol), was used as the reaction medium for step d), it was found that some of the chloro groups in the cyanuric chloride reacted with the methanol to form bis-(tribromophenoxy)-methoxy-s-1,3,5-triazine as an impurity. On the other hand, when acetone or methyl ethyl ketone was used as the organic solvent in step d), the chloro groups were found to react exclusively with the sodium 2,4,6-tribromophenolate despite of the presence of a large amount of water in the reaction mixture which was carried over from the prior bromination step and the prior use of aqueous NaOH to form the sodium 2,4,6-tribromophenolate.

Examples of suitable ketones include acetone, 2-butanone (methyl ethyl ketone), 2-pentanone, 3-pentanone, 3-methyl-2-butanone, 2-hexanone, 3-hexanone, 4-methyl-2-pentanone, 2,4-pentanedione, and their liquid analogs. Methyl ethyl ketone is a preferred ketone, and acetone is the most preferred ketone for use in step d). Other inert organic solvents such as ethers may also be present in the water-ketone media used in the practice of step d) provided such additional solvent does not materially interfere with or otherwise materially impair the desired reaction.

The product when properly prepared pursuant to this invention exists in the form of white, fine solids, and is formed in a yield of at least about 97% and with a purity of at least about 99% by weight. Preferably, the reaction is conducted in a mixture of water and acetone as solvents, and the acetone is recovered and can be, and most preferably, is recycled for use in step d). Another feature of this invention is that white, high purity product can be produced even though phenol of ordinary commercial purity and color is used as the starting material in the process. In short, it is not necessary, although it is permissible, to employ a more expensive high purity, colorless phenol starting material in order to obtain a high quality product.

Isolation of the tris(2,4,6-tribromophenoxy)-s-1,3,5-triazine product is straightforward. Typically, the product precipitates out from the reaction solution to form slurry, from which the solids can be readily recovered by a physical separation procedure such as filtration, decantation, or centrifugation. The solids are then washed, usually with acetone and water, and dried to obtain the product as white powders. Filtration is a preferred separation procedure for isolating the product. Filtration takes place rapidly, and enables a thorough, but relatively fast, water wash to remove the NaCl by-product from the filter cake. As noted above, the waste generated from the process is simply NaCl. This results from the fact that the process enables the recovery of all of the other co-products formed in significant quantities in the process.

The following examples are presented for purposes of illustration and not limitation.

EXAMPLE 1

A 1000-mL flask was charged with 80 g (0.850 mole) of phenol and 240 g of water. At 35–40° C., 416 g of bromine (2.601 moles, 2% excess) was added slowly to the mixture. The temperature was allowed to raise periodically during the feed to keep the brominated phenols in molten form. At end of the feed, the pot temperature was allowed to go up to 100° C. HBr generated from the reaction was dissolved in the water solvent to form hydrobromic acid as a separate layer. After stirring at 100° C. for an hour, the top aqueous HBr layer was removed by siphon and the pot was charged with 240 g of hot water and 5 g of aqueous (35%) hydrazine. The pH of the mixture was adjusted to 7 with diluted caustic, the aqueous layer was removed and the molten mixture was washed with 240 g hot water. With 300 g of acetone the organic layer was transferred to a 2-Liter flask. Analyses by NMR and GC of the acetone solution indicated the purity of 2,4,6-tribromophenol was 99% and the yield was 98%. To this acetone solution was added a 25% of aqueous solution of NaOH (133 g, 0.831 mole) to form sodium tribromophenoxide. While heating the solution at reflux, a solution of cyanuric chloride (46.5 g, 0.2523 mole in 300 g of dry acetone) was added with vigorous stirring, and a mild exothermic reaction was observed during the addition. The slurry was continuously heated at reflux (58° C.) for three hours. After cooling to ambient temperature, the solids were filtered and the cake was thoroughly washed with acetone then water and dried in an aerated oven at 140° C. over a weekend. The cake gave 257 g of tris(2,4,6-tribromophenoxy)-s-1,3,5-triazine as white fine solids of 97% purity. The yield was 96% based on the cyanuric chloride and 85% based on the phenol.

EXAMPLE 2

A 3-Liter flask equipped with an agitator, a thermometer and condenser was charged with 300 g (3.1881 mol) of phenol and 300 g of water. While submerging in a water bath, the flask was fed with 1,000 g (60% of total) of bromine over a period of 30 minutes and the pot temperature was allowed to go up from 23 to 50° C. At this temperature the bath was replaced, and while warming with a mantle, the mixture was fed with the rest of bromine (683 g) over 50 minutes and the temperature was allowed to raise slowly to 100° C. The total bromine fed was 1,683 g (10.521 mol, 10% excess). A portion (58%, 450 g) of the HBr byproduct formed was dissolved in the water and another portion (about 42%, 325 g) was evolved as gas and was scrubbed by a caustic solution. After being cooked at 100° C. for 0.5 hour, the organic layer was analyzed, and was indicated by GC to contain over 98% of 2,4,6-tribromophenol. The upper aqueous HBr layer was removed while hot by a phase cut, and the bottom layer of molten 2,4,6-tribromophenol was treated first with 30 mL of aqueous (35%) hydrazine to convert the red-colored 2,4,6-tribromophenol mixture to an off-white color, and then with 25% caustic to bring the pH to 7. Acetone (900 g) was then added, slowly at beginning, to the hot molten 2,4,6-tribromophenol with stirring. While heating the acetone solution at reflux, 500 g of 25% aqueous caustic solution (which contained 125 g of NaOH, 3.1243 mol, 98% based on phenol) was added to the flask to bring up the pH of the solution to 11–12. Next was added an acetone solution of cyanuric chloride (192 g, 1.0412 mol, 98% based on phenol, in 770 g of dry acetone) over 30 minutes with vigorous agitation (350 RPM). Heating of the resulting slurry was continued at reflux (68° C.) for 1 hour, and then the slurry was cooled to 40° C. and filtered, and the filter cake was washed with acetone (2×, 500 mL each) and then with hot water (2×, 500 mL each). The cake was dried at 140° C. in an aerated oven for 2 days to obtain tris(2,4,6-tribromophenoxy)-s1,3,5-triazine as white, free-flowing, fine particle size solids. The product was formed in a yield of 99% based on cyanuric chloride and 98% based on phenol, and was found by GC analysis to have a purity of 99.6 area percent.

Even though the claims hereinafter may refer to substances, components and/or ingredients in the present tense ("comprises," "is," etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure. Without in any way limiting the generality of the foregoing, although the reaction of step a) specifies bromine as the reactant, it is possible that in the presence of an aqueous medium the actual reactive species in the reaction may be one or more in situ-produced entities such as $HBr_3$ or the like. Irrespective of what actually may take place at the atomic or molecular level, the natural occurrence(s) of using bromine in an aqueous medium is what is to be covered by the ensuing claims; bromine is referred to herein because it is the ingredient that is put into, or initially present in, the aqueous medium.

Each and every patent or publication referred to in any portion of this specification is incorporated in toto into this disclosure by reference, as if fully set forth herein.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for the production of tris(2,4,6-tribromophenoxy)-s-1,3,5-triazine, which process comprises:

a) in an aqueous reaction medium, brominating phenol with bromine under conditions forming an aqueous hydrobromic acid phase and an organic phase consisting essentially of molten 2,4,6-tribromophenol;

b) separating the aqueous hydrobromic acid phase and the molten 2,4,6-tribromophenol from each other, and optionally washing the molten 2,4,6-tribromophenol with an aqueous decolorizing solution;

c) mixing an alkali metal base and water with at least a portion of the 2,4,6-tribromophenol of b) to form an alkali metal salt of tribromophenol; and d) in a mixture consisting essentially of water and at least one liquid ketone, reacting cyanuric chloride with at least a portion of the alkali metal 2,4,6-tribromophenolate of c) such that tris(2,4,6-tribromophenoxy)-s-1,3,5-triazine is produced.

2. A process according to claim 1 wherein at least a), b) and c) are performed in the same reaction vessel without removal of the 2,4,6-tribromophenol therefrom.

3. A process according to claim 2 wherein d) is also performed in the same reaction vessel.

4. A process according to claim 1 wherein in a) bromine is fed portionwise continuously or discontinuously into a mixture of phenol and water, which mixture is initially at a temperature in the range of about 5 to about 110° C., until in the range of about 3.0 to about 3.3 moles of $Br_2$ per mole of phenol have been fed; and wherein the initial ratio of water to phenol is in the range of about 1 to about 10 parts by weight of water per part by weight of phenol.

5. A process according to claim 4 wherein the bromine is fed in the liquid state, and wherein the rate at which the bromine is fed and the temperature of the reaction mixture are controlled such that substantially no bromine vapor is formed in the reaction vessel during substantially the entire reaction period.

6. A process according to claim 5 wherein the reaction temperature during the feed of the first 60% of the bromine is progressively increased from about ambient room temperature to a temperature in the range of about 50 to about 60° C., and during the remaining 40% of said feed the temperature is progressively increased to a temperature in the range of about 90 to about 100° C.

7. A process according to claim 4 wherein said initial ratio of water to phenol is such that essentially no gaseous hydrogen bromide is evolved from the reaction mixture.

8. A process according to claim 7 wherein said initial ratio of water to phenol is about 3:1 on a weight basis.

9. A process according to claim 4 wherein said initial ratio of water to phenol is such that a major portion of the hydrogen bromide co-product exists as aqueous hydrobromic acid and a minor portion of the hydrogen bromide co-product exists as gaseous hydrogen bromide, and said aqueous hydrobromic acid and said gaseous hydrogen bromide are recovered.

10. A process according to claim 9 wherein said initial ratio of water to phenol is about 1:1 on a weight basis.

11. A process according to claim 9 wherein at least a portion of the aqueous hydrobromic acid is used as at least a portion of the aqueous reaction medium employed in a) in the same or in a subsequent reaction.

12. A process according to claim 1 wherein at least a portion of the alkali metal base and water used in c) is a preformed water solution of sodium hydroxide which is used in an amount to bring the pH of resulting mixture to about 7.

13. A process according to claim 1 wherein at least a portion of the alkali metal base and water used in c) is a preformed water solution of potassium hydroxide which is used in an amount to bring the pH of resulting mixture to about 7.

14. A process according to claim 1 wherein at least a portion of the alkali metal base and water used in c) is a preformed water solution of lithium hydroxide which is used in an amount to bring the pH of resulting mixture to about 7.

15. A process according to claim 1 wherein at least a portion of the alkali metal base used in c) is sodium carbonate.

16. A process according to claim 1 wherein at least a portion of the alkali metal base used in c) is potassium carbonate.

17. A process according to claim 1 wherein at least a portion of the alkali metal base used in c) is lithium carbonate.

18. A process according to claim 1 wherein the molten 2,4,6-tribromophenol is washed with aqueous hydrazine or sulfite decolorizing solution before forming the alkali metal salt of the 2,4,6-tribromophenol in c), and wherein said decolorizing solution is an aqueous hydrazine or sulfite solution.

19. A process according to claim 1 wherein the liquid ketone in d) is acetone or methyl ethyl ketone.

20. A process for the production of tris(2,4,6-tribromophenoxy)-s-1,3,5-triazine, which process comprises:

a) feeding liquid bromine portionwise continuously or discontinuously into a mixture of phenol and water in which the initial ratio of water to phenol is in the range of about 1 to about 10 parts by weight of water per part by weight of phenol, while maintaining the resultant reaction mixture at a temperature in the range of about 5 to about 110° C., until in the range of about 3.0 to about 3.3 moles of $Br_2$ per mole of phenol have been fed such that there are formed at least (i) an aqueous hydrobromic acid phase, and (ii) an organic phase consisting essentially of molten 2,4,6-tribromophenol;

b) removing the aqueous hydrobromic acid phase from the molten 2,4,6-tribromophenol, washing the molten 2,4,6-tribromophenol with an aqueous decolorizing solution to reduce the coloration of the 2,4,6-tribromophenol, mixing an aqueous solution of a alkali metal base with the resultant 2,4,6-tribromophenol of reduced coloration in an amount to achieve a pH in the mixture of about 7, and adding a liquid ketone solvent to the resultant neutral mixture;

c) while the neutral mixture is at a temperature in the range of about 80 to about 100° C., mixing therewith an essentially stoichiometric amount based on the initial amount of phenol used in a), of alkali metal base as an aqueous solution thereof to thereby form a solution of alkali metal salt of tribromophenol; and d) while the temperature of the solution of alkali metal salt of tribromophenol is in the range of about 50 to about 90° C., feeding continuously or discontinuously a solution of cyanuric chloride in a liquid ketone until an essentially stoichiometric amount based on the initial amount of phenol used in a) has been fed, and agitating the resultant reaction mixture such that tris(2,4,6-tribromophenoxy)-s-1,3,5-triazine is produced.

21. A process according to claim 20 wherein at least a), b) and c) are performed in the same reaction vessel without removal of the 2,4,6-tribromophenol therefrom.

22. A process according to claim 21 wherein d) is also performed in the same reaction vessel.

23. A process according to claim 20 wherein said initial ratio of water to phenol is such that a portion of the hydrogen bromide co-product in a) exists as said aqueous hydrobromic acid phase and a portion of the hydrogen bromide co-product is gaseous hydrogen bromide; wherein said aqueous hydrobromic acid phase and said gaseous hydrogen bromide are recovered; wherein the aqueous decolorizing solution used in b) is an aqueous solution of hydrazine; wherein the aqueous solution of alkali metal base used in b) is a 5 to 50 wt % aqueous solution of sodium hydroxide; and wherein the liquid ketone solvent used in b) is acetone.

24. A process according to claim 23 wherein said initial ratio of water to phenol is about 1:1 on a weight basis.

25. A process according to claim 20 wherein at least a portion of the aqueous hydrobromic acid is used as at least a portion of the aqueous reaction medium employed in a) of a subsequent reaction.

26. A process according to claim 23 wherein during substantially the entire period of time during which the feed in c) is taking place, the neutral mixture is heated and maintained at reflux temperature.

27. A process according to claim 26 wherein during substantially the entire period of time during which the feed in d) is taking place, the solution of sodium salt of tribromophenol is heated and maintained at reflux temperature.

28. A process according to claim 27 wherein said initial ratio of water to phenol is about 1:1 on a weight basis; and wherein at least a), b) and c) are performed in the same reaction vessel without removal of the 2,4,6-tribromophenol therefrom.

29. A process according to claim 28 wherein at least a portion of the aqueous hydrobromic acid is used as at least a portion of the aqueous reaction medium employed in a) in the same or in a subsequent reaction; and wherein d) is also performed in the same reaction vessel.

* * * * *